United States Patent [19]

Bauman

[11] Patent Number: 5,140,982
[45] Date of Patent: Aug. 25, 1992

[54] RESUSCITATOR

[76] Inventor: Jack Bauman, 2210 Wilshire Blvd., #705, Santa Monica, Calif. 90403

[21] Appl. No.: 487,399

[22] Filed: Mar. 2, 1990

Related U.S. Application Data

[63] Continuation-in-part of Ser. No. 313,157, Feb. 21, 1989, Pat. No. 5,067,487, which is a continuation-in-part of Ser. No. 80,388, Jul. 31, 1987, Pat. No. 4,821,713, which is a continuation-in-part of Ser. No. 912,508, Sep. 29, 1986, abandoned, which is a continuation-in-part of Ser. No. 882,773, Jul. 17, 1986, abandoned.

[51] Int. Cl.⁵ ................................................ A62B 7/00
[52] U.S. Cl. ............................ 128/205.13; 128/205.11; 128/205.23; 128/205.24
[58] Field of Search ................ 128/203.29, 203.24, 128/205.11, 205.13, 205.23, 205.24, 207.14, 203.11, 722, 728; 272/90; 116/266, 20, 270, 273, 335

[56] References Cited

U.S. PATENT DOCUMENTS

| | | |
|---|---|---|
| 2,162,242 | 6/1939 | Branower . |
| 3,417,727 | 12/1968 | Nemes . |
| 3,473,529 | 10/1969 | Wallace . |
| 3,474,785 | 10/1969 | Jansson . |
| 3,530,857 | 9/1970 | Miczka . |
| 3,780,693 | 12/1973 | Parr . |
| 3,827,451 | 8/1974 | Roob . |
| 3,850,171 | 11/1974 | Ball et al. . |
| 3,882,860 | 5/1975 | Frimberger . |
| 3,949,610 | 4/1976 | Pietsch . |
| 4,016,885 | 4/1977 | Bruner . |
| 4,037,595 | 7/1977 | Elam . |
| 4,088,131 | 5/1978 | Elam et al. . |
| 4,106,502 | 8/1978 | Wilson . |
| 4,203,385 | 5/1980 | Mayer et al. . |
| 4,239,038 | 12/1980 | Holmes . |
| 4,249,527 | 2/1981 | Ko et al. . |
| 4,361,107 | 11/1982 | Gereg . |
| 4,444,201 | 4/1984 | Itoh . |
| 4,468,969 | 9/1984 | Schwartz . |
| 4,473,082 | 9/1984 | Gereg . |
| 4,499,846 | 2/1985 | Bergeron et al. . |
| 4,539,985 | 9/1985 | Magrath . |
| 4,821,713 | 4/1989 | Bauman . |
| 5,067,487 | 11/1991 | Bauman ................... 128/205.13 |

FOREIGN PATENT DOCUMENTS

| | | |
|---|---|---|
| 1175514 | 5/1962 | Fed. Rep. of Germany . |
| 1491631 | 4/1970 | Fed. Rep. of Germany . |
| 864140 | 4/1941 | France . |
| 2063687 | 6/1981 | United Kingdom . |
| 2145335 | 3/1985 | United Kingdom . |

Primary Examiner—David Isabella
Assistant Examiner—K. Reichle
Attorney, Agent, or Firm—William W. Haefliger

[57] ABSTRACT

A resuscitator that includes a ventilation mask structure for sealingly surrounding a patient's mouth and nose, a gas flow manifold having passage structure for delivering ventilating gas from a source of the gas to the mask structure, and a manually collapsible gas receptable operatively coupled to the gas flow manifold comprising a modular structure for detecting gas pressure in the manifold; the modular structure including wall structure defining a bore, the modular structure defining a port structure communicating with the gas flow manifold to communicate gas pressure in the manifold to the bore; a plunger slidably mounted to the bore, the plunger having a flange defined thereon; spring structure mounted intermediate the flange of the plunger and wall structure of the modular structure so as to limit movement of the plunger relative to such wall structure of the modular structure; at least a portion of a wall of the wall structure of the modular structure being transparent, wherein such movement of the plunger relative to the transparent wall can be seen exteriorly of the transparent wall and wherein the transparent wall has indicia defined thereon whereby movement of the plunger relative to the indicia on the transparent wall indicates the pressure detected by the plunger.

15 Claims, 8 Drawing Sheets

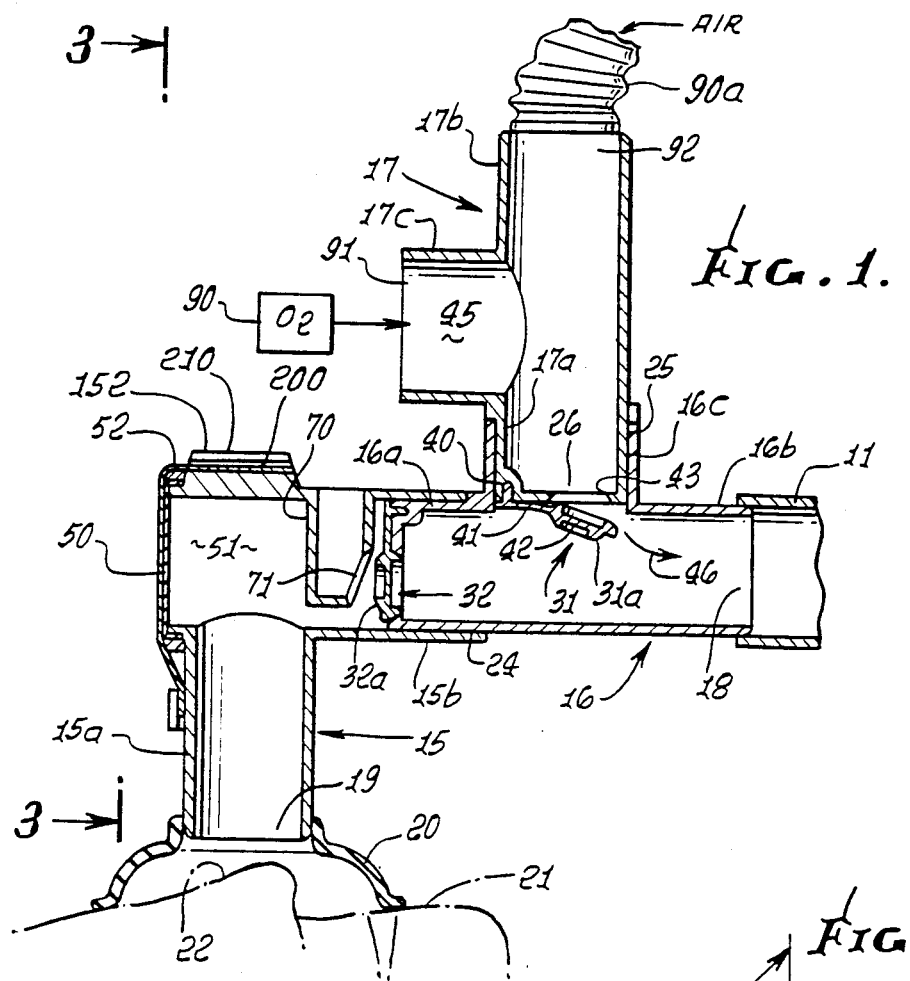
FIG. 1.
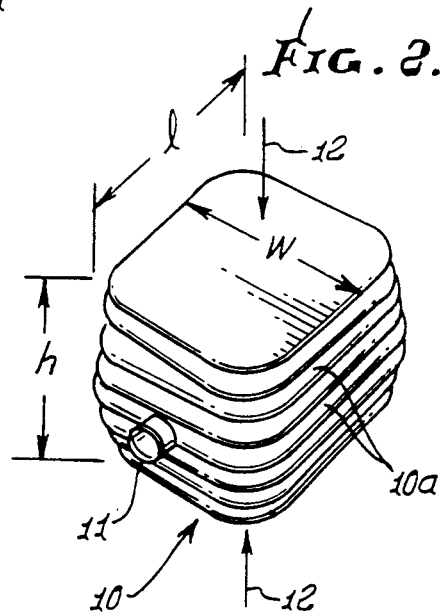
FIG. 2.
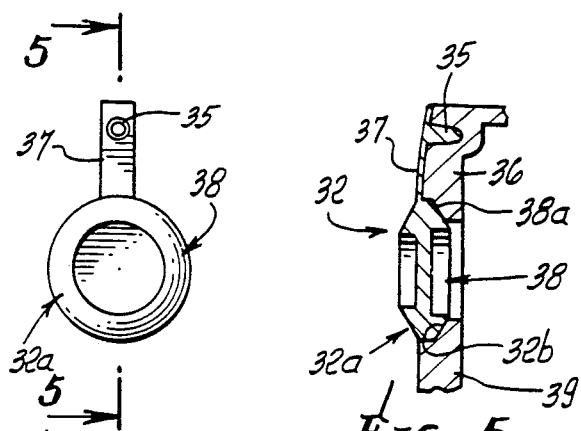
FIG. 4.
FIG. 5.

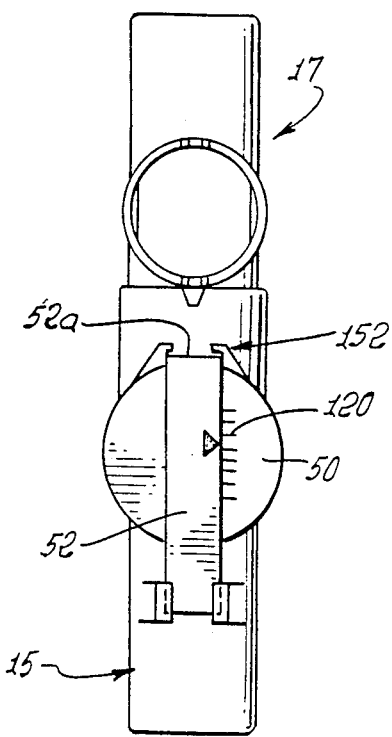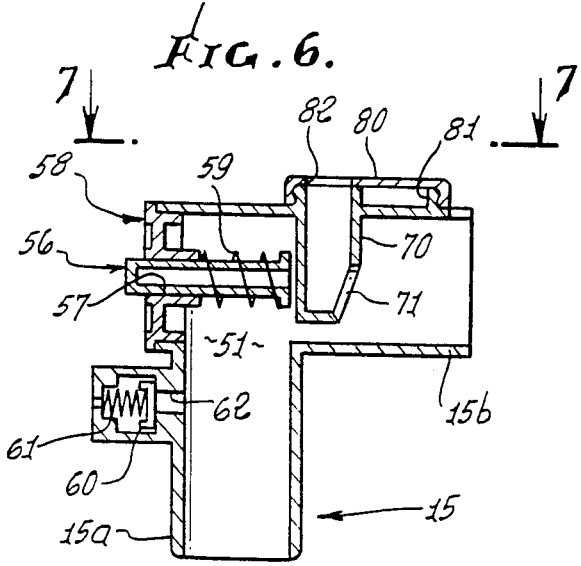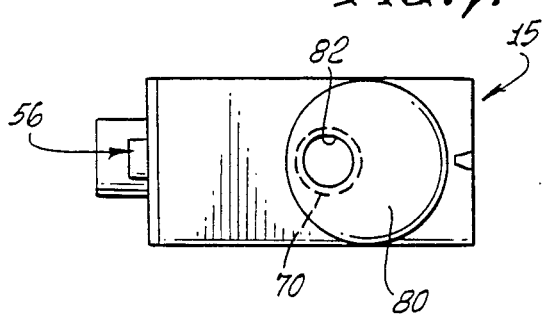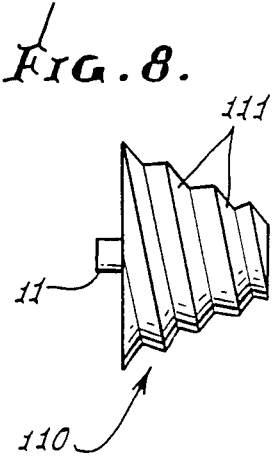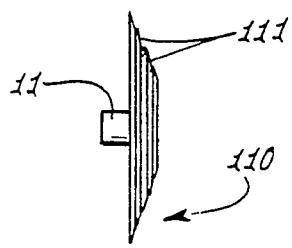

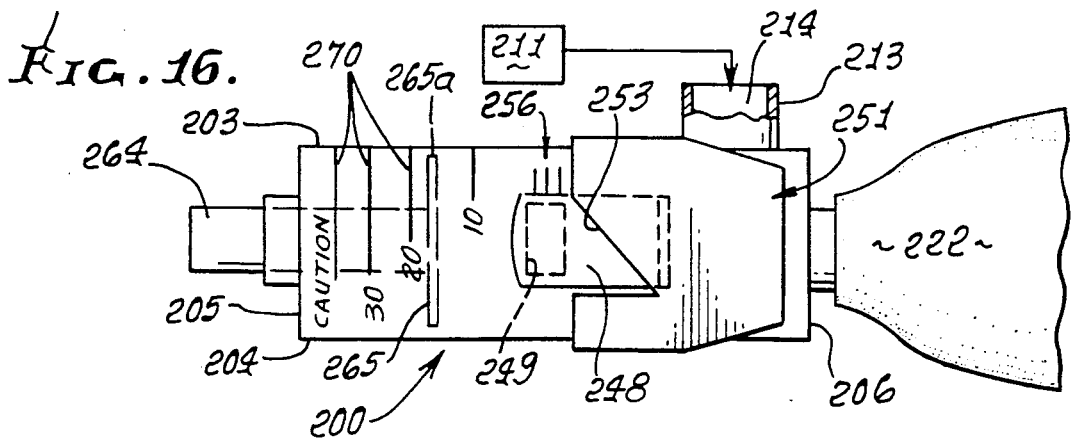
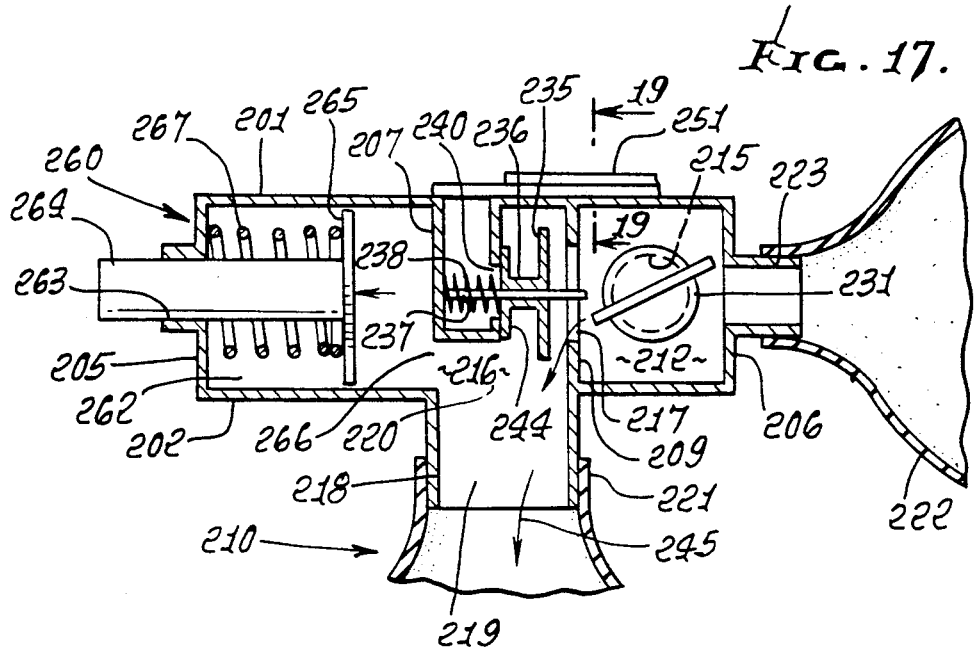
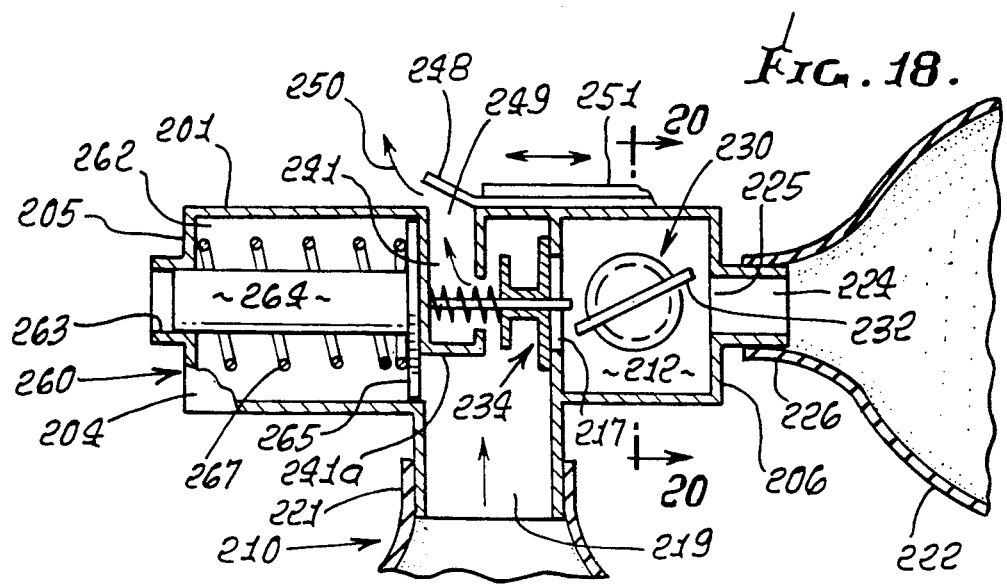

RESUSCITATOR

This is a continuation-in-part of Ser. No. 313,157 filed Feb. 21, 1989, now U.S. Pat. No. 5,067,487, which is a continuation-in-part of Ser. No. 080,388 filed Jul. 31, 1987 (now U.S. Pat. No. 4,821,713), which is a continuation-in-part of Ser. No. 912,508, filed Sep. 29, 1986, now abandoned, which is a continuation-in-part of Ser. No. 882,773, filed Jul. 17, 1986, now abandoned.

BACKGROUND OF THE INVENTION

This invention relates generally to resuscitation of patients, as during heart attacks, shock, fainting, etc.; more particularly, it concerns improved apparatus, characterized by high reliability, simplicity of construction, ease of use and safety against infection, and incorporation of multiple safety measures.

In the past, mouth-to-mouth resuscitation was believed to be necessary to provide required inhalation and exhalation of patients undergoing shock, heat attacks, etc.; however, the risk and danger of infection to the administrator of resuscitation is now recognized as serious, indeed critical, and to be avoided at all times. There is need for a simple, safe, and inexpensive resuscitation apparatus that is capable of easy manual use.

SUMMARY OF THE INVENTION

It is a major object of the invention to provide apparatus meeting the above need. Basically, the resuscitation apparatus of the invention comprises:

a ventilator mask means for sealingly surrounding the patient's mouth and nose;

a gas flow manifold having first, second, and third gas flow passage means for delivering ventilating gas from a source of ventilating gas to the mask means;

means for operatively coupling the third gas flow passage means to the mask means;

a manually collapsible gas receptacle;

means for operatively coupling the manually collapsible gas receptacle to the first gas flow passage means;

the second gas flow passage means being in flow communication with a source of ventilating gas;

the first gas flow passage means being operatively coupled to the third gas flow passage means and the second gas flow passage means being operatively coupled to the first gas flow passage means;

first one-way flow valve means mounted intermediate the second and first gas flow passage means for preventing flow from the first gas flow passage means to the second gas flow passage means and for allowing flow from the second gas flow passage means to the first gas flow passage means;

second one-way flow valve means mounted intermediate the first and third gas flow passage means for preventing flow from the third gas flow passage means to the first gas flow passage means and allowing flow from the first gas flow passage means to the third gas flow passage means;

the first one-way flow valve means and the second one-way flow valve means being mounted so that when the manually collapsible gas receptacle is collapsed, the first one-way flow valve means prevents flow from the first gas flow passage means to the second gas flow passage means and the second one-way flow valve means allows flow from the first gas flow passage means to the third gas flow passage means and, when the manually collapsible gas receptacle expands, the first one-way flow valve means allows flow from the second gas flow passage means to the first gas flow passage means and the second one-way flow valve means prevents flow from the third gas flow passage means to the first gas flow passage means;

the third gas flow passage means including gas outlet means and means for closing the gas outlet means when the second one-way flow valve means allows flow from the first to the third gas flow passage means; and air escape means mounted to a wall member of at least one of the first and third flow passage means having manually adjustable air vent means for controlling the amount of air passing from the third gas flow passage means through the gas outlet means when the second one-way flow valve means prevents flow from the third gas flow passage means to the first gas flow passage means.

As will be seen, the air vent means comprises an air bleed flap valve, controlling an opening in the wall member. Also, the air bleed flap valve typically extends generally parallel to the wall member, and the manually adjustable air vent means includes a manually adjustably movable slider means slidably carried by the manifold to be slidable in closely overlying relation to the air bleed flap valve to control movement of the flap valve away from the opening in the wall member. Further, the slider means advantageously has a control edge means angled relative to the direction of adjustable movement of the slider means for controlling the degree of flexing of the flap valve member.

Another object is the provision of gas flow manifold which further includes means for detecting air pressure within the third gas flow passage means and for defining a portion of a wall of the third ga flow passage means; and a wall of the third gas flow passage means having means for indicating the pressure detected by the air pressure detecting means.

As will be seen, a bore is typically defined in a wall of the manifold, the means for detecting air pressure and for defining a portion of a wall of the third gas flow passage means comprising a plunger slidably mounted in the bore, the plunger having a flange defined thereon, a spring means mounted intermediate the flange of the plunger and the wall of the manifold so as to limit movement of the plunger relative to the wall of the manifold, at least a portion of a wall integral with the third gas flow passage means being transparent such that movement of the plunger relative to the transparent wall can be seen exteriorly of the transparent wall and wherein the transparent wall has indicia defined thereon whereby movement of the plunger relative to the indicia on the transparent wall indicates the pressure detected by the plunger.

These and other objects and advantages of the invention, as well as the details of an illustrative embodiment, will be more fully understood from the following specification and drawings, in which:

DRAWING DESCRIPTION

FIG. 1 is a section showing interconnected tubing sections and associated flap valves;

FIG. 2 is a perspective view of a collapsible air receptacle connectible to the FIG. 1 tubing sections;

FIG. 3 is an end view of lines 3—3 of FIG. 1;

FIG. 4 is an enlarged frontal view of a valve flapper;

FIG. 5 is a section taken on lines 5—5 of FIG. 4;

FIG. 6 is a section showing a modified tubing section;

FIG. 7 is a top plan view taken on lines 7—7 of FIG. 6;

FIG. 8 is a view showing an alternative collapsible receptacle;

FIG. 9 shows that receptacle in collapsed condition;

FIG. 16 is an enlarged top plan view in lines 16—16 of FIG. 15;

FIG. 17 is an enlarged section taken on lines 17—17 of FIG. 15 during air flow to the mask;

FIG. 18 is a view like FIG. 17 showing position of elements during exhalation via the mask;

DETAILED DESCRIPTION

Figure 10:
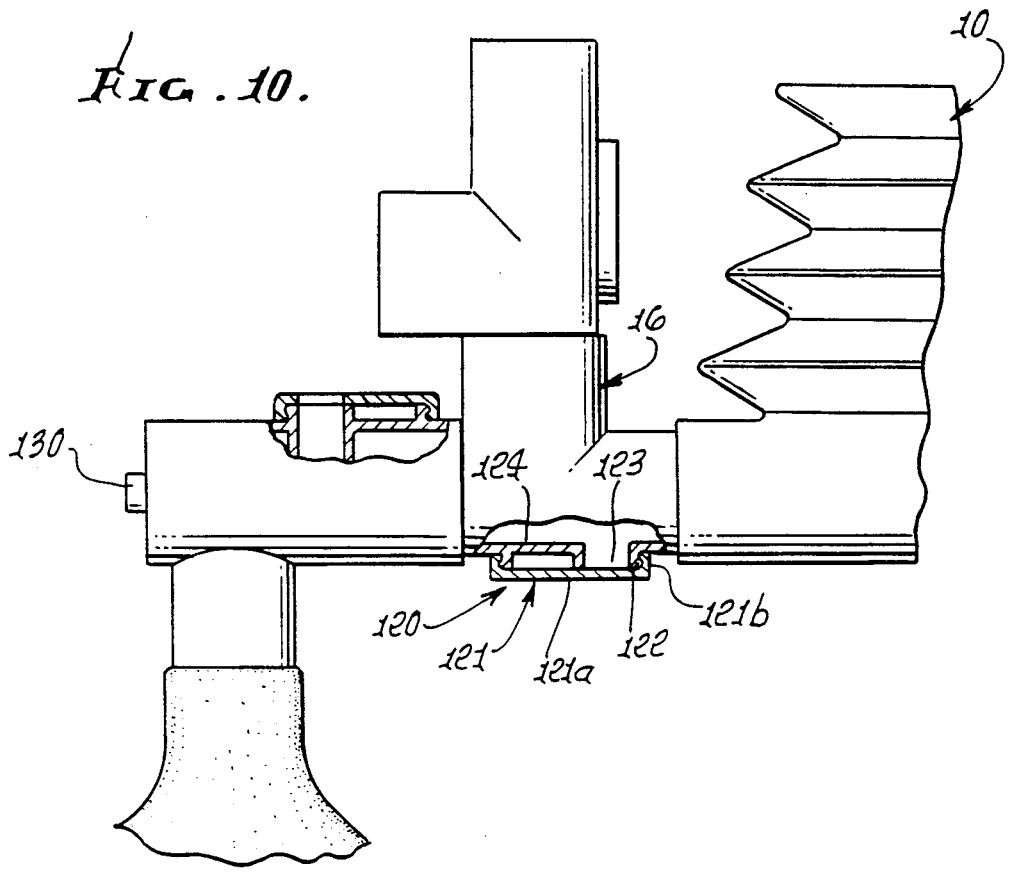
FIG. 10 is a fragmentary side elevation showing provision of air bleed means.

In FIGS. 1 and 2, a manually collapsible air receptacle 10 has an air discharge inlet and outlet 11 attached to a tubing assembly The receptacle has a bellow-like configuration to be easily hand held, and collapsed endwise, in a direction indicated by arrow 12. Note accordion-like pleats 10a. The receptacle may have height "h", length "l", and width "w" dimensions for convenient hand manipulation about as follows:

h = height 4 inches
l = about 4 inches
w = about 4 inches

Almost complete collapse of the receptacle can thereby be achieved.

The tubing assembly includes first, second and third tubular sections 15, 16, and 17, joined together in series, as shown. The assembly defines air inlet means, as at 18, connectible in air passing relation with the receptacle inlet and outlet 11, and an air inlet and outlet 19 connectible in air passing relation with a mask 20 configured to be placed against the patient's face 21, for supplying air to the patient as via his nose 22 for resuscitation. As shown, tubular section 15 is elbow shaped, and has tubular legs 15a and 15b; and sections 16 and 17 are alike and have tee shape. Their likeness enables reduction in molding costs, all sections consisting of molded plastic, for example. Section 16 has tubular legs 16a and 16b, and tubular stem 16c, leg 16a having telescopic interfit at 24 with leg 15b. Section 17 has tubular legs 17a and 17b, and tubular stem 17c. Leg 17a has telescopic interfit at 25 with stem 16c. Thus, the side opening of second section 16, defined by stem 16c, registers with the end opening 26 defined by leg 17a of third section 17. The telescopic interfits at 24 and 26 may be suitably bonded together to provide rigid connections.

Also provided are first and second flap valves generally indicated at 31 and 32, and positioned in at least one tubing section, so that the first flap valve 31 opens and passes intake air to the receptacle to inflate the same when the second flap valve is closed; and so that the second flap valve 32 opens while simultaneously closing opening 71, and passes air from the receptacle (upon squeezing thereof) to the mask 20 via outlet 19, and while flap valve 31 is closed. In this regard, the flap valves typically include normally closed flaps 31a and 32a, the latter illustrated in closed position in FIG. 1, and flap 31a illustrated in open position in that view. FIGS. 4 and show flap 32a as having an anchor 35 penetrating and cemented to wall portion 36 of tubular section 16; a thin cantilevered flat spring arm 37, and disc 38 carried by the arm and annularly tapered at 38a to fit its annular seat 32b in wall 39, when the valve is closed. Valve flapper 31a is similarly configured, with parts 40, 41, 42, and 43 corresponding to parts 35, 37, 38, and 39. The flapper may consist of DELRIN ® plastic material, for example.

When the receptacle 10 is allowed to expand (after its forcible compression), inflating air enters side inlet 45 in section 17, opens flap valve 31, and flows to the receptacle, as indicated by arrow 46. At this time, flap valve 32 is closed. When the receptacle is squeezed, flap valve 31 closes, and valve 32 opens while simultaneously closing 31 to pass air to outlet 19 and to the mask 20 to resuscitate the patient.

Air pressure indicator means may be carried by the tubular section assembly to indicate the extent of pressure build up between valve 32 and outlet 19. In the example shown in FIG. 1, the indicator comprises a movable pressure sensitive part in the form of a balloon membrane 50 exposed to the interior 51 of the elbow, and an indicator such as a slider 52 attached to the membrane. Increased pressure at 51 expands the membrane 50 to the left in FIG. 1, pushing the slider 52 to the left. Indicia at 200 on slider leg 52a variably register with edge 152a of retainer 152 as the leg moves leftwardly. A visible indication of pressure increase is thereby achieved, and indicia 210 on the slider retainer 152 may indicate the degree of pressure increase, on a marker as the slider moves past the indicia 210. In FIGS. 6 and 7, the indicator takes the form of a plunger 56 slidable in a bore 57 formed by an insert 58 attached to the elbow. The extent of plunger travel to the left, resisted by a spring 59, indicates the extent of pressure build up at 51.

A safety valve may be provided to allow escape of excess pressure so that injury to the lungs of a patient may be prevented. As shown, a check valve part 60 is urged by spring 61 to close outlet 62. Part 60 is pushed open by excess air pressure to allow air escape.

Also shown in FIG. 1 is a re-entrant duct 70 extending into leg 15b of section 15. It defines an air discharge port 71 that is open to communicate with the air outlet 19 upon exhalation by the patient, flap valve 32 then being closed against seat 32b. Exhaled lung air then escapes via duct 70. Alternately, port 71 is closed by flap 32a when the second flap valve 32 is open to allow air to flow from the squeezed receptacle to the mask 20. Flap 32a thus performs two functions. Note that air may flow about the re-entrant duct in each position of the flap 32a for minimum flow restriction.

In FIGS. 6 and 7, an enlarged cap 80 controls the effective size of discharge port 7 by controlling the escape of air from the re-entrant duct 70. To this end, the cap 80 fits annularly over an annular neck 81 on the leg 16b; and the cap has an opening 82 thereon that variably registers with the duct 70 as the cap is rotated on the enlarged neck. This serves as a control for air escape upon natural exhalation by the patient, so that positive end expiratory pressure (PEEP) may be achieved if desired.

In FIG. 1, a source of oxygen 90 may be connected with the inlet 45 so that supplied $O_2$ enters via inlet 91 for flow to the receptacle mixing with air supplied to inlet 92 with optional reservoir tubing 90a and later to the patient. More particularly, a reservoir tubing 90a which has a first opened end connectible to tube section 17b and a second end (not shown) spaced from this coupling. The remote end of the oxygen reservoir is preferably an open end to allow free flow of air thereinto when necessary. When valve 31 is closed, for example when collapsible receptacle 10 is being manually compressed to ventilate the patient, the oxygen flow into the inlet 45 will nevertheless continue due to the continuous flow of oxygen from the oxygen source 90. Because valve 31 is closed, the oxygen fed into inlet 45 will tend to flow throughout tubular section 17 and up into reservoir 90a. Then, when the collapsible reservoir 10 is released and valve 32 closes, valve 31 will again open and the oxygen which has begun to fill the oxygen reservoir 90a will be drawn down into tube section 16 and into the collapsible reservoir 10. Thus, the provision of an extension tube 90a to collect oxygen delivered to tubular section 17 while valve 31 is closed constitutes an oxygen reservoir and enables collected oxygen to be fed to the collapsible reservoir when it is refilled.

An oxygen flow rate of as little as 8 liters per minute will supply 100% oxygen to the patient. Section 17 has end opening 92 in communication with tubing 90a.

FIG. 8 shows an alternative conical-shaped receptacle 110 for air or oxygen for use in place of receptacle 10. Its pleats 111 allow its complete endwise collapse, manually, as shown in FIG. 9. Thus, maximal air discharge is achieved; and also high compactness is achieved for storage, as in a user's pocket.

In FIG. 10 the elements are as previously described, except as follows: the second tubular section 16 carries air bleed means, generally indicated at 120, for controlling the amount of air passing to the mask, irrespective of the amount of manual collapse of the receptacle 10. The functioning is such that the user may repeatedly collapse and expand the receptacle 10 without exerting excessive air pressure on the lungs of the patient.

For this purpose, the air bleed means includes manually adjustable air vent structure, as, for example, a stopper having multiple selected positions associated with different vent openings past or through the stopper. FIGS. 11a-11d show the stopper in the form of a rotor or rotatable cap 121 having an end wall 121a and a skirt 121b grippingly interfitting an annular lip 122 on the section 16. Lip 122 surrounds a smaller vent opening 123 through wall 124 of section 16.

The end wall 121a has different sized vent openings 125-127 therein, spaced about axis 129 of rotation, and of selectively larger size to be selectively and individually brought into registration with vent opening 123. Region 128 of the rotor has no vent opening therein, and as shown in rotor position of FIG. 11a, it covers the vent 123 in wall 124. Such position would be used when maximum air flow and pressure to the patient is desired In the rotor position of FIG. 11b, minimum air flow to the patient (such as a baby) is desired, and maximum venting via 123 and 127 is effected (some air of course passing to the patient via the flap valves, as described previously).

Figure 11:
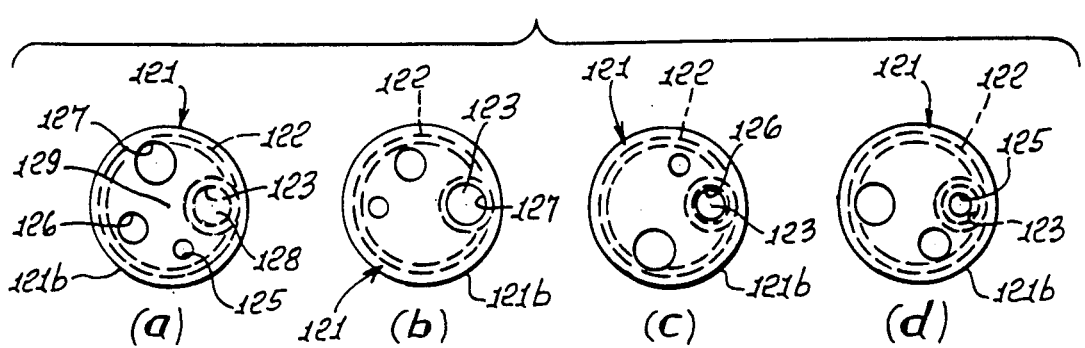
FIGS. 11a–11d are views of an air bleed rotor in different selected positions.

In FIGS. 1c and 11d, intermediate positioning of the rotor, lesser by-pass venting occurs, as for children, smaller adults, etc. Vent openings may be covered by an elastomeric flap to function as check valves, if desired, the construction being like that of FIGS. 4 and 5.

Figure 12:
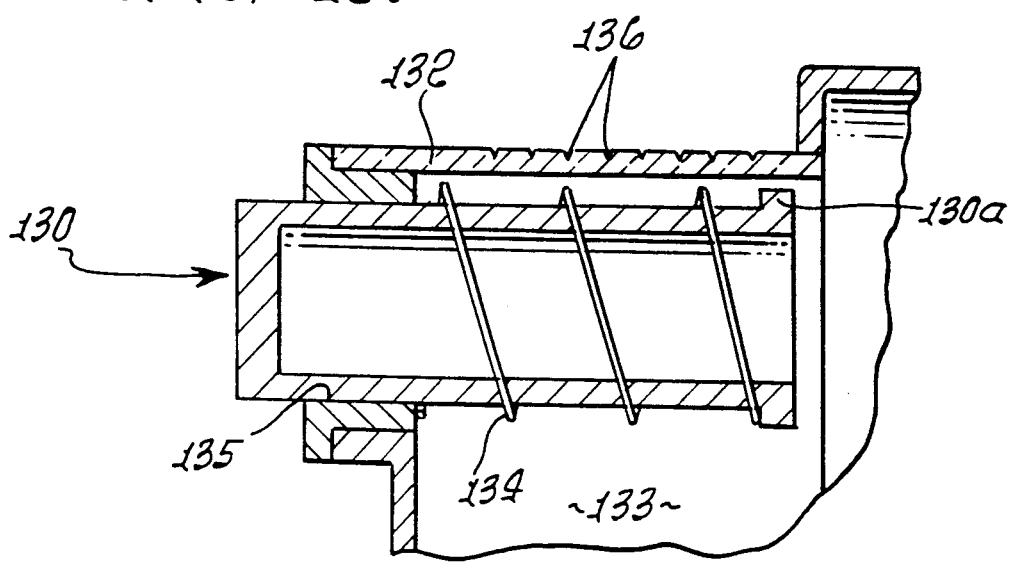
FIG. 12 and 13 are fragmentary side elevations showing pressure build-up sensing structures.

FIG. 12 shows a plunger 130 corresponding to plunger 56 in FIG. 6, except that plunger 130 is of larger diameter, so that its end flange 130a (or other marker thereon) extends or moves closely adjacent to a transparent wall 132 of a tubular section. The latter carries indicia with which the flange 130a is variably registrable as the plunger moves endwise (i.e., pressure build up in interior 133, and the plunger moves leftwardly as resisted by light spring 134). Guide bore 135 is provided for guiding plunger movement.

The indicia referred to may take the form of markings 136 on the transparent wall, as shown, so that as the plunger moves, the registration of the flange 130a with different markings is indicating changes in pressure build up. Spring 134 returns the plunger rightwardly as pressure drops in space 133.

Figure 13:
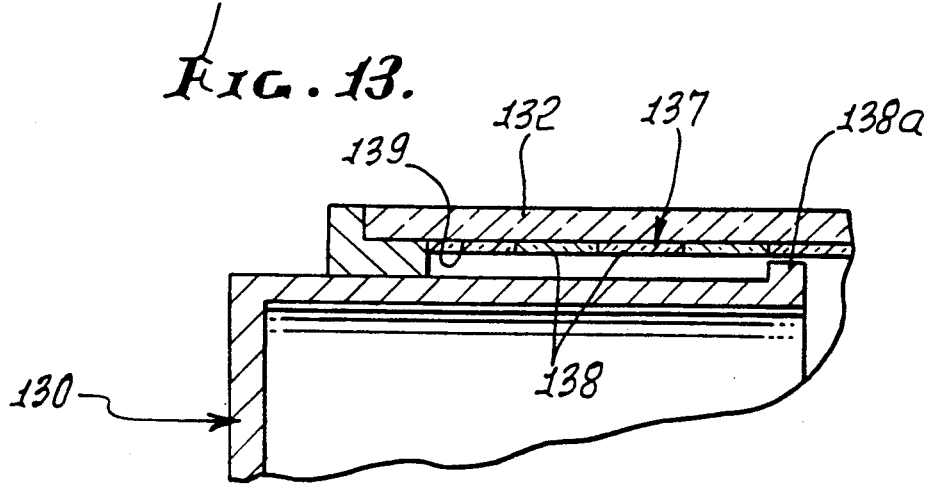
Figure 14:
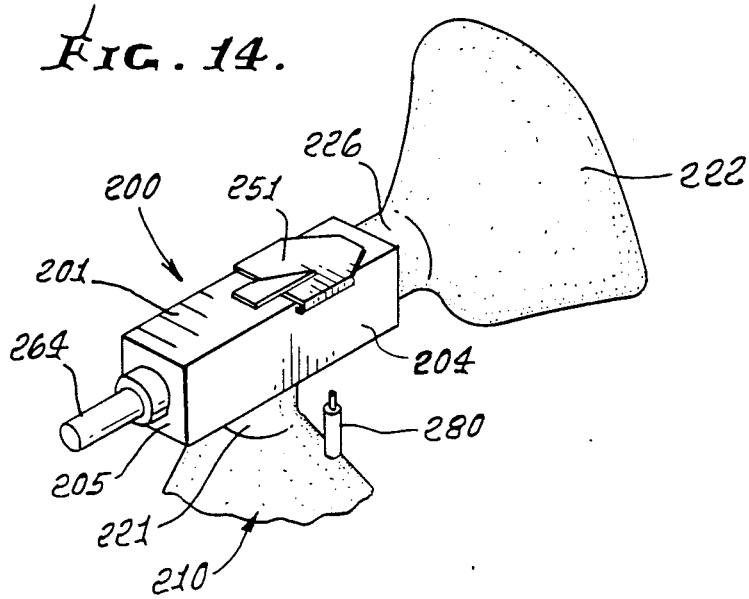
FIG. 14 is a perspective view of a modified form of the invention.
Figure 15:
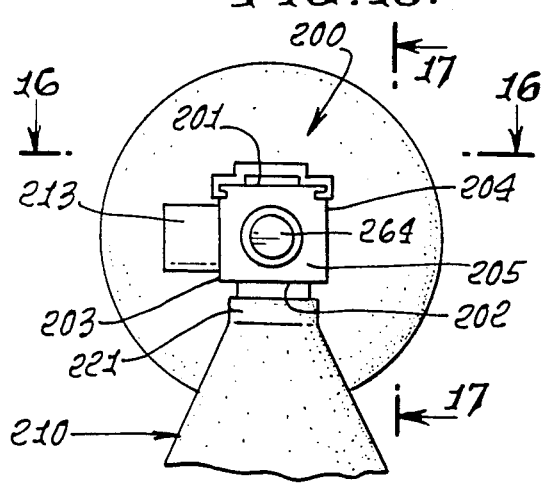
FIG. 15 is an end view of the FIG. 14 apparatus.

FIG. 13 shows the provision of color coded indicator means 137. It is in the form of a lengthwise color coded semi-transparent sleeve 138 fitting against the bore 139 defined by wall 132. Thus, as flange 138a moves left and right, it variably registers with the different color codes on the sleeve, all of which is visible through transparent wall 132.

FIGS. 14-20 show a modified version of the invention, wherein an improved air bleed means is provided, and a modified air flow controlling valve system is incorporated.

In general organization, a box-like gas flow manifold means 200 is forwardly longitudinally elongated, and has top, bottom, side, and end walls 201-206. Upright transverse walls 207-209 are provided within the interior of the manifold.

A mask is provided at 210, seen in FIG. 17, and a source of ventilating gas appears at 211, in FIG. 16. The manifold means 200 has first, second, and third gas flow passage means for controllably delivering ventilating gas from source 211 to the mask 210. The first gas flow passage means typically includes those walls that extend about passage 212; the second gas flow passage means typically includes side duct 213 connected to wall 203 to flow ventilating gas from passage 214 through an aperture 231 in wall 203 into passage 212; and the third gas flow passage means typically includes the walls that extend about passage 216. An aperture 217 in wall 209 passes gas from passage 212 to passage 216.

Means for operatively coupling the third passage 216 to the mask means typically includes a bottom duct 218 connected to bottom wall 202 to provide a passage 219 that communicates, through open aperture 220 in wall 202, with passage 216. The mask has a neck 221 that fits over the duct 218. A manually collapsible gas receptacle 222 is provided; and a means for operatively coupling that receptacle to the first gas flow passage means typically includes an end duct 223 connected to end wall 206 to provide a passage 224 that communicates, through open aperture 225 in wall 201, with passage 212. The receptacle has a neck 226 that fits over and is attached to the duct 223.

It will be seen that the first gas flow passage means (defining first passage 212) is operatively coupled to the third gas flow passage means (defining third passage 216); and that the second gas flow passage means (defining passage 214) is operatively coupled to the first gas flow passage means (defining passage 212).

Figure 20:
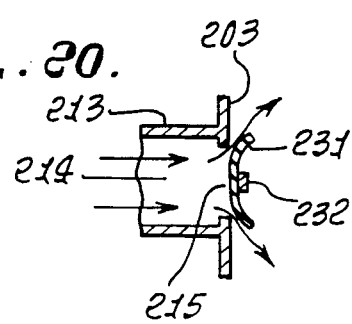
FIG. 20 is a section in lines 20—20 of FIG. 18.

A first one-way flow valve means 230 is mounted intermediate the second and first gas flow passage means for preventing flow from the first gas flow passage means to the second gas flow passage means, and for allowing flow from the second gas flow passage means to the first gas flow passage means. The means 230 is shown in FIG. 20 to include the flap valve disc 231 mounted at the inner side of wall 203 to control aperture 206. A bar 232 is attached at its apparatus ends to wall 203 and extends across and attaches to the inner side of flap valve disc 231. Thus, the bar allows resilient flexing of the disc 231, as shown, as ventilating gas flow from passage 214 to passage 212 and into the receptacle 222 as it expands; but the disc closes against the wall 203 to close aperture 206 and prevent gas flow from passage 212 to passage 214 when the gas receptacle is squeezed. Flap disc 231 may consist of resilient rubber, or the like.

A second one-way flow valve means 234 is mounted intermediate the first and third gas flow passage means for preventing flow from the third gas flow passage means to the first gas flow passage means (as during exhalation from the user's lungs, via mask 210), and for allowing flow from the first gas flow passage means to the third gas flow passage means, as during squeezing of the receptacle 222. The means 234 is shown in FIGS. 17 and 18 to include the relatively stiff valve disc 235 mounted at the left side of internal wall 209 to control aperture 217. Disc 235 is mounted on a tubular hub 236 slidable left and right on a stem 237. The latter is attached to wall 207 and projects to the right, centrally through aperture 217. A coil spring 238 surrounds the stem and is endwise compressed between the hub 236 and the wall 207 to constantly urge the hub and disc 235 toward wall 209. When sufficient gas pressure exists in passage 212 (as a result of squeezing of the receptacle 222), the spring force is overcome and the disc 235 moves leftwardly away from aperture 217 to allow gas to flow from 212 to 216, and via 219 to the mask interior.

Thus, it will be seen that the first one-way flow valve means and the second one-way flow valve means are mounted so that when the manually collapsible gas receptacle is collapsed, the first one-way flow valve means prevents flow from the first gas flow passage means to the second gas flow passage means, and the second one-way flow valve means allows flow from the first gas flow passage means to the third gas flow passage means; and, when the manually collapsible gas receptacle expands, the first one-way flow valve means allows flow from the second gas flow passage means to the first gas flow passage means, and the second one-way flow valve means prevents flow from the third gas flow passage means to the first gas flow passage means.

The above referenced third gas flow passage means includes gas outlet means, as for example is represented by aperture 240 in wall 209 and re-entrant channel 241 between walls 207 and 208, and above lower wall 241a connecting the lower ends of walls 207 and 208. Note that spring 238 passes through the aperture 240 in FIG. 18 (showing exhalation mode). Means is provided for closing the gas outlet means when the second one-way flow valve means allows flow from the first to the third gas flow passage means (see FIG. 17 and arrows 225). Such means for closing the gas outlet means typically comprises a relatively stiff valve disc 244 mounted on sleeve 236 for movement therewith, and between internal walls 208 and 209. In FIG. 17, the disc 244 is held leftwardly against wall 208 surrounding aperture 240 by gas pressure exerted leftwardly against discs 235 and 244. This closes aperture 240.

Also provided is air bleed or escape means mounted to a wall of at least one of the first and third gas flow passage means, and having manually adjustable air vent means for controlling the amount or flow of air passing from the third gas flow passage means through the outlet means, when the second one-way flow valve means prevents flow from the third passage 216 to the first passage 212 (see FIG. 18 mode of operation). The air vent means typically comprises an air bleed flap mans (typically consisting of rubber) 248 at the outer side of a wall member such as wall 201, controlling a vent opening 249 in that wall member. Note in FIG. 18 the resilient lifting of the flap means 248 due to gas flow escape from 216 to 241, indicated by arrows 250. The air bleed flap valve means 248 illustrated extends generally parallel to the wall member 201 in undeflected state (see FIG. 17); and the manually adjustable air vent means illustrated includes a manually adjustable movable slider means 251, slidably carried by the manifold to be slidable along wall 201 in closely overlying relation to the air bleed flap valve means for controlling the extent of lifting movement of the flap valve means away from the opening 249. This in turn controls the resistance to exhalation to provide adjustable expiratory resistance (PEEP).

It will be noted that the resiliently flexible flap means 248 operates as if a spring were incorporated; however, no extra spring is required. It provides what may be called a "PEEP" valve, i.e., to provide 'positive end expiratory pressure'. It controls expiratory air pressure, as distinguished from air volume, in the sense that positive pressure on the patient's or user's lung is maintained. Such positive pressure prevents lung collapse.

Figure 19:
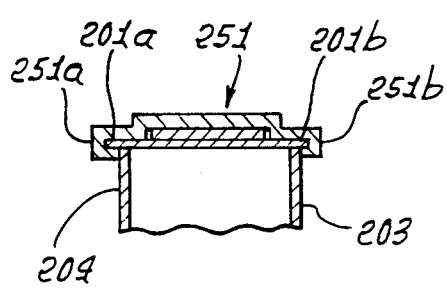
FIG. 19 is a section on lines 19—19 of FIG. 17.

FIG. 19 shows the slider plate means 251 to have in-turned, U-shaped edge portions 251a and 251b slidably gripping the projecting edges 201a and 201b of top wall 201. Also, the thumb controllable slider has control edge means 253 angled as shown, i.e., between 30° and 60°, relative to the forward (leftward in FIG. 16) direction of slider movement for controlling the extent of upward flexing of the flap relative to the opening 249. The angle of edge 253 requires that the slider be moved leftwardly through a greater or extended range "d" of movement from initial edge overlap of opening 249 (than if edge 253 were parallel to wall 207) to complete edge overlap of opening 249, giving a higher degree of flap control per increment of slider sliding. Indicia 256 on the top wall 201, progressively overlapped by the slider, provide variable registry as the slider is moved for accurate position setting of the slider relative to the air bleed flap valve means.

The gas flow manifold shown further includes a means for detecting air or gas pressure within the third gas flow passage 216, such means generally indicated at 260. It is integrated with the structure shown, and typically with portion of a wall (such as walls 207, 201 and 202) of the third gas flow passage means. Note that walls 201, 202, 203, and 204 are extended forwardly (leftwardly) from regions 216 and 249 to provide a plunger chamber 262. A bore 263 is defined in end wall 205 of the manifold, and the means for detecting air or gas pressure comprising a plunger 264 slidably mounted in that bore, so as to be variably extendable outwardly to the left of wall 205. The plunger has a flange 265 on its rightward end to engage wall 207 and cover an aperture 266 between passage 216 and chamber 262 in FIG. 18 position. A coil spring 267 is mounted or positioned intermediate flange 265 and wall 205 so as to resist and limit leftward movement of the plunger due to air or gas pressure exertion on the rightward face of flange 265, that pressure communicated from passage 216 (see FIG. 17). Thus the extent of leftward displacement of the flange 225 (and of the plunger) is determined by the pressure in passage 216.

At least a portion of top wall 201 is transparent, such that movement of the plunger relative to the wall 201 can be seen exteriorly of that wall 201; and that wall typically has indicia 270 defined thereon whereby movement of the plunger relative to the indicia indicates the pressure detected by the plunger. Note that the flange 265 has a top edge 265a closely underlying different of the indicia 270 as the plunger moves. Air or gas may leak at bore 263 to allow leftward movement of the flange 265. The indicia may typically comprise a plurality of colored translucent segments, and/or a series of numbers indicating pressure detected by the plunger.

The receptacle 222 typically comprises a squeezably hollow, resilient rubber bag, or a bellows element having folds for allowing the bellows to substantially completely collapse.

The mask 210 may carry a pressure safety valve 280 adapted to open if gas pressure in the mask reaches a predetermined level.

Figure 21:
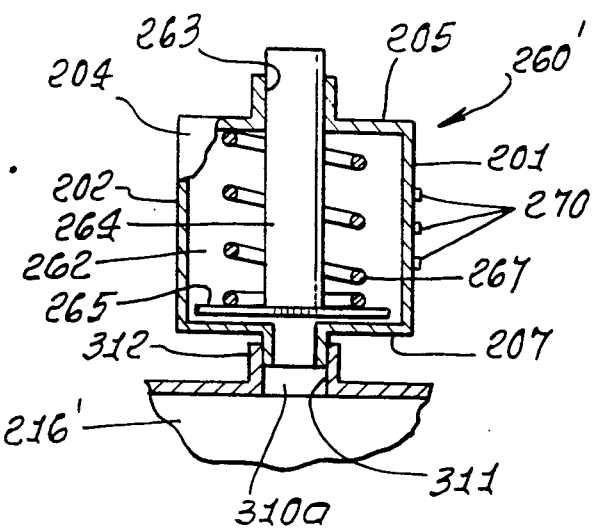
FIGS. 21-23 show modifications.

FIG. 21 illustrates a modular means 260', closely similar to the means 260 in FIG. 18 for detecting air or gas pressure within a gas flow passage 216'. Elements the same as those in FIG. 18 bear the same numerals. Integral with end wall 207 is a nipple 310 that defines a port 310a. That port communicates the passage 216' with the pressure receiving side of flange 265. Nipple 310 is attachable to, or fits in, bore 311 in a wall 312 of the remaining structure that forms passage 216'. Thus, the modular means 260' forms a self-contained, modular, box-like unit that may be replaced, or removed, or added, as desired. It may thus be employed as an air pressure detector with other types of resuscitators.

Figure 22:
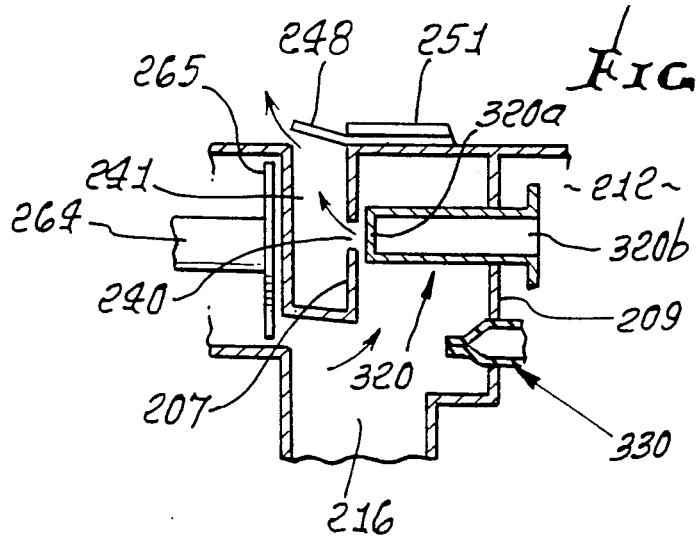

In FIG. 22, structure is shown that is substituted for the one-way flow valve means 234 seen in FIG. 18, other elements being the same as in FIG. 18; however, spring 238 is eliminated. Aperture 240 on wall 244 is controlled by closed end 320a of a hollow plunger 320, slidably in bore 217a defined by aperture 217 (the latter aperture also seen in FIG. 18). The open end 320b of the plunger is exposed to gas pressure in passage 212.

A duck bill one-way check valve 330, as for example consisting of rubber, is carried by wall 209 to project leftwardly into passage 216. When the receptacle 222 is squeezed, air pressure developed in passage 212 pushes the plunger 320 leftwardly so that plunger end 320a closes port 240. Also, such air pressure is exerted on check valve 330, so that air flows through that valve into passage 216 and to the mask 210 and to the patient's lungs. As the patient subsequently breathes outwardly, check valve 330 closes, and plunger 320 is forced rightwardly by pressure on end wall 320a. This opens port 240, so that air is expelled at 241 and past air bleed "PEEP" flap valve 248.

Figure 23:
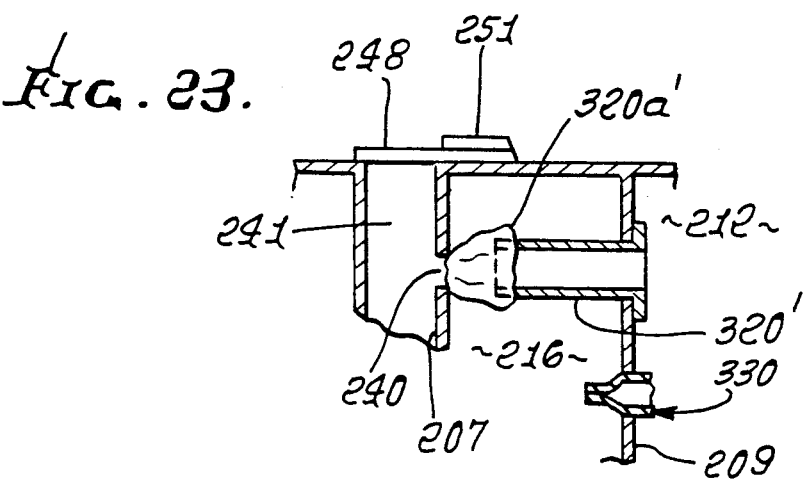

In FIG. 23, the modified closed end wall 320a' (corresponding to closed end wall 320a of the plunger 320) is a flexible bag. The tube 320' (corresponding to plunger 320) is fixed to wall 209. As the user squeezes the receptacle 222 and pressure rises in 212, the bag 320a' expands to engage and close the port 240. Later, when the patient breathes outwardly externally, the gas pressure in 216 collapses the bag 320a' rightwardly thus opening the port 240 to allow expulsion of air (breath) via passage 241 and flap valve 248. Port 240 may be bounded by a rubber O-ring and seal against the flexible bag. Otherwise, the structure of FIG. 21 is like that of FIG. 20.

Figure 24:
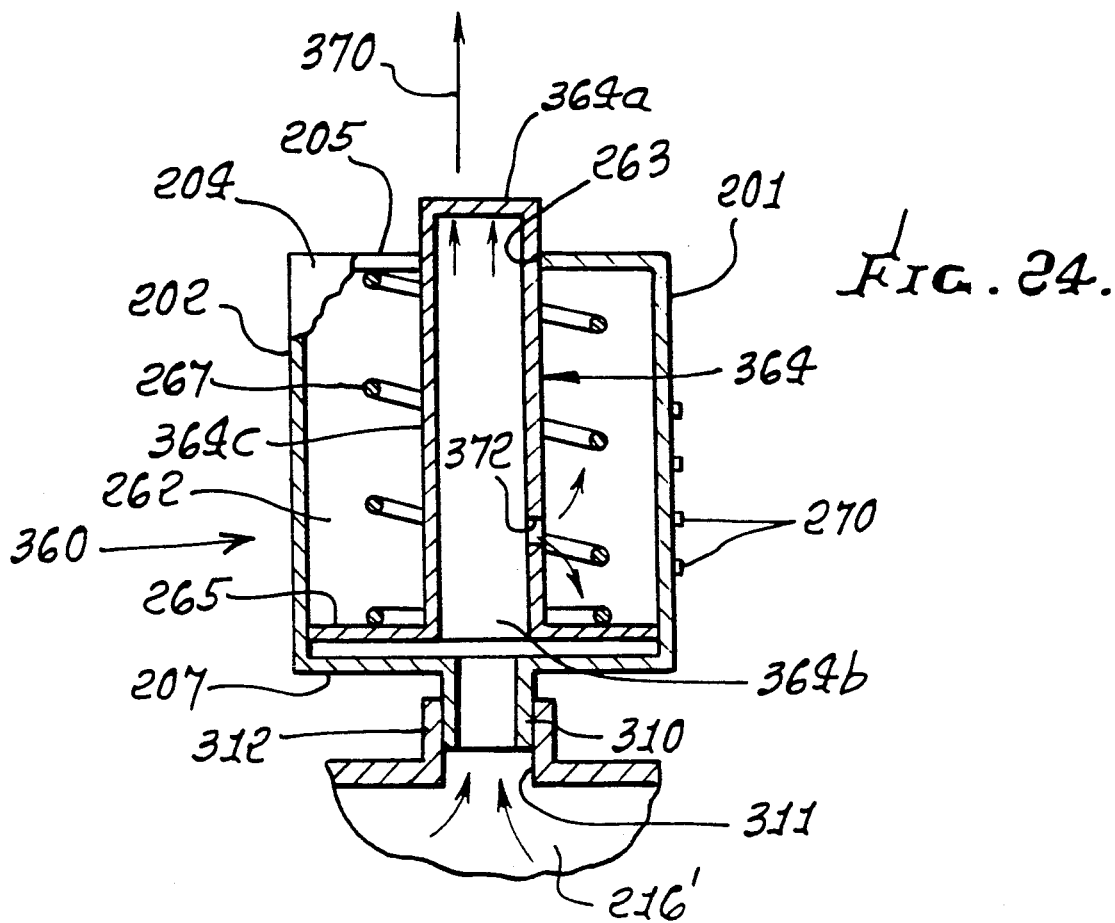
FIG. 24 is a view like FIG. 21 showing a modification.

Referring to FIG. 24, the modular means 360 is closely similar to the structure of FIG. 21, corresponding elements bearing the same identifying numerals. The modified plunger 364 is tubular, and has a closed outer end at 364a, and an open inner end at 364b that receives the pressure of air in manifold passage 216' associated with resuscitator structure, for example as is described above. If sufficient air pressure builds up, it urges the plunger in the direction of arrow 370 by pressure exertion against plunger end wall 364a.

Figure 25:
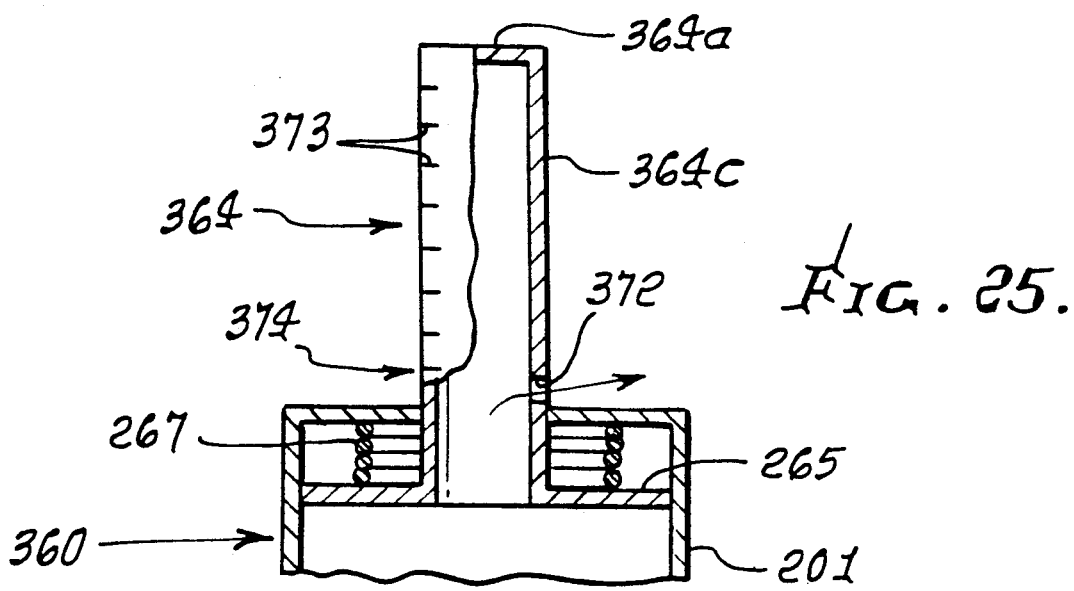
FIG. 25 is a view like FIG. 24 showing pressure release.

The cylindrical wall 364c of the plunger has a throughport 372 positioned to release gas (air) pressure in the manifold passage 216' to the exterior (see FIG. 25) only after the plunger has compressed spring 267 to predetermined extent. This corresponds to a top limit (safe) pressure level, which pressure generated by the squeezable receptacle 10 cannot then exceed. Accordingly, the plunger serves two functions, i.e., a manifold pressure indicating (manometer) function is served by indicia 373 on the plunger that progressively appears at 374 as such pressure increases, and also a pressure relief (safety) function, as by releasing excess manifold pressure to the exterior via port 372, as described.

I claim:

1. A modular device for detecting gas pressure for use with a resuscitator of the type which includes a ventilation mask means for sealingly surrounding a patient's mouth and nose, a gas flow manifold having passage means for delivering ventilating gas from a source of said gas to said mask means, and a manually collapsible gas receptacle operatively coupled to said gas flow manifold, for detecting gas pressure in the resuscitator, the modular device comprising:

a) wall means defining a bore,
   b) communicating port means for providing fluid communication with the gas flow manifold to communicate gas pressure in the manifold to said bore,
   c) a plunger slidably mounted in said bore, the plunger having a flange defined thereon,
   d) spring means mounted intermediate said flange of said plunger and said wall means so as to resist movement of the plunger relative to said walls means,
   e) at least a portion of said wall means being transparent, whereby movement of said plunger relative to said transparent wall can be seen exteriorly of said transparent wall and wherein said transparent wall has indicia defined thereon whereby movement of said plunger relative to the indicia on said transparent wall indicates the pressure in said bore between said communicating port means and said plunger.

2. The modular device of claim 1 wherein said wall means further defines plunger port means at an end of said bore, said plunger including a tubular wall segment extending from said flange element so that at least a portion of said plunger is hollow, said plunger having a closed end remote from said flange which projects at least partially into said plunger port means, said plunger being slidably disposed in said bore so that as said plunger slides in response to gas pressure communicated with said bore through said communicating port means, said plunger projects to a greater extent through said plunger port means, and including a hole defined through said tubular wall segment of said plunger so that when said plunger projects sufficiently through said plunger port means, said hole is exposed to the exterior of said wall means whereby gas can be released from said bore to the exterior of said wall means.

3. The modular device of claim 2 wherein said tubular wall segment is round in cross-section.

4. The modular device of claim 1 wherein said modular means comprises a manometer, and wherein said plunger is hollow and has a closed end that projects from the exterior of said manifold.

5. The modular device of claim 1 in combination with a said resuscitator.

6. The modular device of claim 5 wherein said resuscitator includes:

said manifold having walls defining first, second and third gas flow passage means for delivering ventilating gas from the source of ventilating gas to said mask means;

means for operatively coupling said third gas flow passage means to said mask means;

means for operatively coupling said manually collapsible gas receptacle to said first gas flow passage means;

said second gas flow passage means being in flow communication with the source of ventilating gas;

said first gas flow passage means being operatively coupled to said third gas flow passage means and said second gas flow passage means being operatively coupled to said first gas flow passage means;

first one-way flow valve means mounted intermediate said second and first gas flow passage means for preventing flow from said first gas flow passage means to said second gas flow passage means and for allowing flow from said second gas flow passage means to said first gas flow passage means;

second one-way flow valve means mounted intermediate said first and third gas flow passage means for preventing flow from said third gas flow passage means to said first gas flow passage means and allowing flow from said first gas flow passage means to said third gas flow passage means;

said first one-way flow valve means and said second one-way flow valve means being mounted so that when said manually collapsible gas receptacle is collapsed, said first one-way flow valve means prevents flow from said first gas flow passage means to said second gas flow passage means and said second one-way flow valve means allows flow from said first gas flow passage means to said third gas flow passage means and, when said manually collapsible gas receptacle expands, said first one-way flow valve means allows flow from said second gas flow passage means to said first gas flow passage means and said second one-way flow valve means prevents flow from said third gas flow passage means to said first gas flow passage means;

said third gas flow passage means including gas outlet means and means for closing said gas outlet means when said second one-way flow valve means allows flow from said first to said third gas flow passage means; and air escape means including an opening defined in a said wall of at least one of said first and third flow passage means having manually adjustable air vent means for controlling the flow of air passing from said third gas flow passage means through said gas outlet means when said second one-way flow valve means prevents flow from said third gas flow passage means to said first gas flow passage means, thereby providing end expiratory pressure, PEEP.

7. A modular device, as defined in claim 6, wherein said air vent means comprises an air bleed flap valve controlling a size of said opening in said wall.

8. A modular device, as defined in claim 7, wherein said air bleed flap valve extends generally parallel to said wall and said manually adjustable air vent means includes a manually adjustably movable slider means slidably carried by said manifold to be slidable in closely overlying relation to said air bleed flap valve to control movement of the flap valve away from said opening in said wall.

9. A modular device, as defined in claim 8, including indicia on one of the said slider means and wall means to variably register as the slider member is adjustably moved relative to the air bleed flap valve.

10. A modular device, as defined in claim 9, wherein said slider means has control edge means angled relative to the direction of adjustable movement of the slider means for controlling the degree of flexing of the air bleed flap valve member.

11. A modular device, as defined in claim 6, wherein said first one-way flow valve means and said air vent means each comprise a flap valve.

12. A modular device, as defined in claim 6, wherein said gas outlet means comprises an aperture defined through a wall of said third gas flow passage means, and said second one-way flow valve means allows flow from said first to said third gas flow passage means, when said second one-way flow valve means closes said aperture.

13. A modular device, as defined in claim 6, wherein said wall means further defines plunger port means at an end of said bore, said plunger including a tubular wall segment extending from said flange element so that at least a portion of said plunger is hollow, said plunger having a closed end remote from said flange which projects at least partially into said plunger port means, said plunger being slidably disposed in said bore so that as said plunger slides in response to gas pressure communicated with said bore through said communicating port means, said plunger projects to a greater extent through said plunger port means, and including a hole defined through said tubular wall segment of said plunger so that when said plunger projects sufficiently through said plunger port means, said hole is exposed to the exterior of said wall means whereby gas can be released from said bore to the exterior of said wall means.

14. The modular device of claim 13 wherein said tubular wall segment is round in cross-section.

15. A modular device for detecting gas pressure for use in a resuscitator of the type which includes a ventilation mask means for sealingly surrounding a patient's mouth and nose, a gas flow manifold having passage means for delivering ventilating gas from a source of said gas to said mask means, and a manually collapsible gas receptacle operatively coupled to said gas flow manifold, for detecting gas pressure in the resuscitator, the modular device comprising:

a) wall means defining a bore, b) communicating port means for providing fluid communication with the gas flow manifold to communicate gas pressure in the manifold to said bore,
c) a plunger slidably mounted in said bore, the plunger having a flange defined thereon, said plunger including a tubular wall segment extending from said flange element so that at least a portion of said plunger is hollow, said plunger having a closed end remote from said flange,
d) spring means mounted intermediate said flange of said plunger and said wall means so as to yieldably resist movement of the plunger relative to said walls means, and
e) plunger port means at an end of said bore, said closed end of said plunger projecting at least partially into said plunger port means, said plunger being slidably disposed in said bore so that as said plunger slides in response to gas pressure communicated with said bore through said communicating port means, said plunger projects to a greater extent through said plunger port means, and including a hole defined through said tubular wall segment of said plunger so that when said plunger projects sufficiently through said plunger port means, said hole is exposed to the exterior of said wall means whereby gas can be released from said bore to the exterior of said wall means.

* * * * *